(12) United States Patent
Falk et al.

(10) Patent No.: US 8,163,784 B2
(45) Date of Patent: Apr. 24, 2012

(54) BIOCIDAL COMPOSITIONS

(75) Inventors: Uwe Falk, Bruchköbel (DE); Michael Marcus Walter, Liederbach (DE)

(73) Assignee: Clariant Produkte (Deutschland) GmbH, Frankfurt am Main (DE)

( * ) Notice: Subject to any disclaimer, the term of this patent is extended or adjusted under 35 U.S.C. 154(b) by 428 days.

(21) Appl. No.: 11/992,210

(22) PCT Filed: Sep. 6, 2006

(86) PCT No.: PCT/EP2006/008667
§ 371 (c)(1),
(2), (4) Date: Mar. 25, 2009

(87) PCT Pub. No.: WO2007/033764
PCT Pub. Date: Mar. 29, 2007

(65) Prior Publication Data
US 2009/0203756 A1    Aug. 13, 2009

(30) Foreign Application Priority Data
Sep. 21, 2005   (DE) .......................... 10 2005 045 002

(51) Int. Cl.
*A61K 31/425*    (2006.01)
(52) U.S. Cl. ...................................... 514/373
(58) Field of Classification Search .................. 514/373
See application file for complete search history.

(56) References Cited

U.S. PATENT DOCUMENTS

| | | | |
|---|---|---|---|
| 3,689,660 A | 9/1972 | Burk et al. | |
| 4,272,636 A | 6/1981 | Thompson et al. | |
| 4,624,972 A | 11/1986 | Nace | |
| 4,708,720 A | 11/1987 | Grangette et al. | |
| 5,147,884 A | 9/1992 | Diehl et al. | |
| 5,153,213 A | 10/1992 | Schmidt | |
| 5,276,047 A | 1/1994 | Eggensperger et al. | |
| 5,753,016 A * | 5/1998 | Hayashi et al. | 106/31.48 |
| 6,080,706 A | 6/2000 | Blanvalet et al. | |
| 6,228,382 B1 | 5/2001 | Lindner et al. | |
| 6,355,752 B1 | 3/2002 | Brungs et al. | |
| 6,376,696 B1 | 4/2002 | Raab et al. | |
| 6,437,068 B2 | 8/2002 | Loeffler et al. | |
| 6,511,946 B1 | 1/2003 | Theis et al. | |
| 6,802,893 B1 * | 10/2004 | Komatsu et al. | 106/31.6 |
| 6,805,735 B2 * | 10/2004 | Taniguchi et al. | 106/31.13 |
| 2006/0099157 A1 | 5/2006 | Dahms | |
| 2009/0105320 A1 | 4/2009 | Falk et al. | |

FOREIGN PATENT DOCUMENTS

| | | |
|---|---|---|
| CA | 1189343 | 6/1985 |
| DE | 3604521 | 8/1986 |
| DE | 19508654 | 9/1996 |
| DE | 19548710 | 6/1997 |
| DE | 19636114 | 3/1998 |
| DE | 19651351 | 6/1998 |
| DE | 19928127 | 5/2000 |
| EP | 0503175 | 9/1992 |
| EP | 0824144 | 2/1998 |
| EP | 1028129 | 8/2000 |
| EP | 1122286 | 8/2001 |
| EP | 1290943 | 3/2003 |
| EP | 1116733 | 4/2003 |
| EP | 1060142 | 5/2003 |
| GB | 2250737 | 6/1992 |
| GB | 2298791 | 9/1996 |
| JP | 10 114605 | 5/1998 |
| JP | 2004 051711 | 2/2004 |
| JP | 2004 123905 | 4/2004 |
| WO | WO91/07395 | 5/1991 |
| WO | WO00/06675 | 2/2000 |
| WO | WO0141570 | 6/2001 |
| WO | WO02050225 | 6/2002 |
| WO | WO02067685 | 9/2002 |
| WO | WO03106592 | 12/2003 |

OTHER PUBLICATIONS

Research Disclosure for "452015 Composition", Dec. 2001.
English Abstract for DE19548710, 1997.
English Abstract for DE19636114, 1988.
English Abstract for JP 2004 051711, 2004.
English Abstract for JP 2004 123905, 2004.
WPI English Abstract for JP 10 114605, 1998.
EPODOC English Abstract for JP 10 114605, 1998.
International Search Report for PCT/EP2006/008667, 2006.
Translation of International Preliminary Examination Report for PCT/EP2006/008667, 2006.
U.S. Environmental Proctection Agency: Inert (other) Ingredients in Pesticide Products—Categorized List of Inert (other) Pesticide Ingredients. List 3, http://ww.epa.gob/opprd001/inerts/inertslist3cas.pdf, 2006.
German Office Action for DE 10 2005 045 002.4, 2005.

* cited by examiner

*Primary Examiner* — Rei-tsang Shiao
(74) *Attorney, Agent, or Firm* — Tod A. Waldrop

(57) ABSTRACT

The present invention relates to biocidal compositions comprising at least one biocidal active substance and at least one solvent from the group of polyglycol monobutyl ethers, and to their use as preservatives and disinfectants. More specifically, the invention provides compositions comprising
a) at least one biocidal active substance
b) at least one solvent according to the formula I $$R-(O-CH_2-CH_2)_x-O-H \qquad (I)$$

in which
R is a linear or branched butyl group and
x is a number from 3 to 10.

7 Claims, No Drawings

BIOCIDAL COMPOSITIONS

The present invention relates to biocidal compositions comprising at least one biocidal active substance and at least one solvent from the group of polyglycol monobutyl ethers, and to their use as preservatives and disinfectants.

Biocides are used in very diverse fields of application in order to control or prevent the growth of microorganisms, and thus to ensure the preservation of products and materials. Important fields of application are the preservation of acrylic paints or water-based adhesives, or surface treatment.

High requirements are placed on biocidal formulations with regard to the chemical and physical stability under extreme thermal conditions for long storage times. Even at temperatures below 0° C., phase separation, the crystallizing out of individual ingredients, and gel formation should not occur.

In numerous specifications, the use of butyl ethers for dissolving biocides is disclosed.

In DE-A-36 04 521, monobutyl ethers of ethylene glycol are used in biocidal formulations.

WO 2001/041 570 discloses compositions which comprise bactericides and fungicides dissolved in diethylene glycol butyl ether. The use of diethylene glycol butyl ether as solvent in biocidal formulations is also disclosed in EP-A-1 290 943, WO-02/067 685 and GB-2 250 737.

WO-02/50225 discloses the use of propylene glycol mono-n-butyl ether as solvent for biocidal active substances.

DE-A-199 28 127 discloses a method of producing siloxane quats in which singly and doubly terminally capped glycols are used as solvents in the reaction.

Both monoethylene glycol and diethylene glycol butyl ethers have the tendency to form crystals at temperatures below 0° C.

It was therefore the object of the present invention to find solvents which are able to readily dissolve the biocidal active substances, are toxicologically and ecotoxicologically acceptable, and do not exhibit crystal or gel formation even at temperatures below 0° C.

Surprisingly, it has now been found that certain toxicologically and ecotoxicologically acceptable glycols from the group of polyglycol monobutyl ethers are able to dissolve a large number of biocidal active substances, improve the compatibility of ingredients of biocidal formulations (biocidal active substance(s), adjuvants, dispersants, electrolytes etc.) with very different physicochemical properties, are stable even under considerable thermal stress and prevent the biocidal active substance from crystallizing out at low temperatures. The viscosity behavior of the biocidal formulations comprising polyglycol monobutyl ether at temperatures below 0° C. is very advantageous.

The invention therefore provides compositions comprising
a) at least one biocidal active substance
b) at least one solvent according to the formula I $$R-(O-CH_2-CH_2)_x-O-H \quad (I)$$

in which
R is a linear or branched butyl group and
x is a number from 3 to 10.

The invention further provides the use of the butyl polyglycol ethers according to formula I as solvent for at least one biocidal active substance.

The invention further provides a method of producing a solution of at least one biocidal active substance by dissolving the biocidal active substance in one or more butyl polyglycol ether(s) of the formula I.

R is preferably n-butyl.
x is preferably a number from 3 to 6.

In addition, in a preferred embodiment, R is n-butyl and x is a number from 3 to 6 at the same time.

In a further preferred embodiment, the compound of the formula I is a mixture which comprises 50% by weight or more, preferably 60% by weight or more, particularly preferably 70% by weight or more, of triethylene glycol butyl ether and 10% by weight or more, preferably 15% by weight or more, of tetraethylene glycol butyl ether. In addition, particular preference is given to this embodiment with an n-butyl radical.

It is also preferred that the compound of the formula 1 comprises less than 20% by weight, preferably less than 10% by weight, in particular less than 5% by weight, specifically less than 3% by weight, of diethylene glycol butyl ether.

In a further preferred embodiment, the compounds of the formula I have a boiling point greater than or equal to 240° C., or, if mixtures of compounds of the formula I are used, a boiling range above 240° C.

For the purposes of this invention, biocidal active substance is any substance which is able to kill microorganisms, such as bacteria, algae or fungi. Biocidal effectiveness is the ability of a biocidal active substance to kill microorganisms, such as bacteria, algae or fungi.

Preferred biocidal active substances are isothiazolines and derivatives thereof. Isothiazolines (which below include their derivatives) are understood as meaning compounds with the structural unit

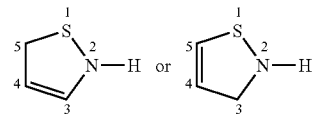

and derivatives thereof which may carry substituents at positions 2, 3, 4 and/or 5. Such substituents may, for example, be linear, branched or cyclic hydrocarbon groups, halogen atoms or carbonyl groups. Preferred hydrocarbon groups are $C_1$- to $C_{12}$-alkyl groups, phenyl groups and condensed aromatic systems.

Further preferred derivatives of isothiazoline are isothiazolinones of the formula

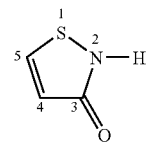

which may carry substituents like the isothiazolines described above.

Isothiazolines with biocidal effectiveness are, for example, nonhalogenated isothiazolines. Suitable nonhalogenated isothiazolines are, for example, 2-methyl-3-isothiazoline, 2-methyl-4-isothiazolin-3-one, 2-ethyl-3-isothiazoline, 2-propyl-3-isothiazoline, 2-isopropyl-3-isothiazoline, 2-butyl-3-isothiazoline (in which butyl may be n-butyl, isobutyl or tert-butyl), 2-n-octyl-3-isothiazoline, 2-octyl-4-isothiazolin-3-one or 1,2-benzoisothiazolin-3-one or its alkali metal or ammonium salt.

Isothiazolines with biocidal effectiveness are, for example, halogenated isothiazolines. Suitable halogenated isothiazolines are, for example, 5-chloro-2-methyl-3-isothiazoline, 5-chloro-2-methyl-4-isothiazolin-3-one or 4,5-dichloro-2-(n-octyl)-4-isothiazolin-3-one.

The preferred isothiazoline is 1,2-benzoisothiazolin-3-one and/or its alkali metal or ammonium salt, in particular its sodium salt.

1,2-Benzoisothiazolin-3-one Corresponds to the Formula

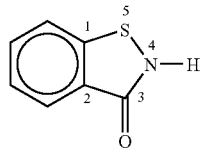

In a preferred embodiment of the invention, more than one isothiazoline is dissolved in butyl polyglycol ethers according to formula (I). This may preferably be a mixture of 2 nonhalogenated isothiazolines, or a mixture of one nonhalogenated isothiazoline and one halogenated isothiazoline.

In a particularly preferred embodiment of the invention, 1,2-benzoisothiazolin-3-one and/or the 1,2-benzoisothiazolin-3-one alkali metal salt or ammonium salt, in particular the sodium salt, is dissolved in a butyl polyglycol ether according to the formula (I), the solution being prepared by homogenizing a solution, heated to about 60-70° C., of butyl polyglycol ether according to the formula (I) and alkali metal or ammonium hydroxide with 1,2-benzoisothiazolin-3-one to give a clear solution, where the molar ratio of 1,2-benzoisothiazolin-3-one to the hydroxide is in the range from 1:0.5 to 1.5, preferably 1:0.6 to 1.2, particularly preferably 1:0.75-1.05.

In a preferred embodiment, besides at least one isothiazoline, the compositions according to the invention can comprise at least one further biocidal active substance which is not an isothiazoline. Preferred further biocidal active substances are triazines, for example 1,3,5-tris(2-hydroxyethyl)hexahydro-S-triazine, 1,5-trimethyl-[2H,4H,6H]-hexahydro-1,3,5-S-triazine, methylenebismorpholine, oxazolidine, 3-iodo-2-propynyl butylcarbamate, 2-bromo-2-nitropropanediol, glutaraldehyde, glutardialdehyde, sodium 2-pyridinethiol 1-oxide, p-hydroxybenzoic alkyl esters, tris(hydroxymethyl)nitromethane, dimethyloldimethylhydantoin, 1,6-dihydroxy-2,5-dioxahexane; 1,2-dibromo-2,4-dicyanobutane; 3-(3,4-dichlorophenyl)-1,1-di-methylurea (diurone); N-cyclopropyl-N'-(1,1-dimethylethyl)-6-(methylthio)-1,3,5-triazine-2,4-diamine; methylbenzimidazol-2-yl carbamate (carbendazim); N-(1,1-dimethylethyl)-N'-ethyl-6-(methylthio)-1,3,5-triazine-2,4-diamine(terbutryn); 4-chloro-3,5-dimethylphenol; 2,4-dichloro-3,5-dimethylphenol; 2-benzyl-4-chlorophenol; 2,2'-dihydroxy-5,5'-di-chlorodiphenylmethane; p-tertiary-amylphenol; o-phenylphenol; sodium o-phenyl-phenol; p-chloro-m-cresol; 2-(thiocyanomethylthio)benzothiazole; 3,4,4'-trichloro-carbanilide; 1-hydroxy-2-pyridinethione-zinc; 1-(4-chlorophenyl)-4,4-dimethyl-3-(1H-1,2,4-triazol-1-ylmethyl)pentan-3-ol (tebuconazole),1-[2-(2,4-dichlorophenyl)-4-propyl-1,3-dioxolan-2-ylmethyl)-1H-1,2,4-triazole (propiconazole), 3-iodo-2-propynylbutyl carbamate, 2-bromo-2-nitropropanediol, formaldehyde; urea; glyoxal; 2,2'-dithiobis(pyridine N-oxide), 3,4,4-trimethyloxazolidine, 4,4-dimethyloxazolidine, N-hydroxymethyl-N-methyldithiocarbamate, potassium salt adamantane, N-trichloromethylthiophthalimide, 2,4,5,6-tetrachloroisophthalonitrile, 2,4,5-trichloro-phenol, dehydroacetic acid, copper naphthenate, copper octoate, tributyltin oxide, zinc naphthenate, copper 8-quinolate.

Further suitable are biocides from the group of quaternary ammonium compounds, preferably alkyldimethylammonium chlorides, such as, for example, coconut dimethylammonium chloride, dialkyldimethylammonium chlorides, such as, for example, dicoconut dimethylammonium chloride, alkyldimethylbenzylammonium chlorides, such as, for example, $C_{12/14}$-dimethylbenzylammonium chloride or coconut dimethyldichlorobenzylammonium chloride.

The invention preferably provides compositions comprising
a) at least one isothiazoline with biocidal effectiveness in weight amounts of from 10% to 60%, preferably 30% to 55%, particularly preferably 40% to 52%, based on the biocidal composition, and
b) a solvent according to formula I.

The invention further preferably provides compositions comprising
a) at least one nonhalogenated isothiazoline with biocidal effectiveness in weight amounts of from 10% to 60%, preferably 30% to 55%, particularly preferably 40% to 52%, based on the biocidal composition, and
b) at least one halogenated isothiazoline with biocidal effectiveness in weight amounts of from 0.1 to 15% by weight, preferably 0.2 to 10% by weight, particularly preferably 0.3 to 5% by weight, based on the biocidal composition, and
c) a solvent according to formula I.

The invention further preferably provides compositions comprising
a) at least one nonhalogenated isothiazoline with biocidal effectiveness in weight amounts of from 10% to 60%, preferably 30% to 55%, particularly preferably 40% to 52%, based on the biocidal composition, and
b) at least one halogenated isothiazoline with biocidal effectiveness in weight amounts of from 0.1% by weight to 15% by weight, preferably 0.2% by weight to 10% by weight, particularly preferably 0.3% by weight to 5% by weight, based on the biocidal composition,
c) at least one further biocidal active substance in weight amounts of from 3 to 15% by weight, preferably 7 to 13% by weight, particularly preferably 9 to 12% by weight, based on the biocidal composition, and
c) a solvent according to formula I.

The invention further preferably provides compositions comprising
a) 1,2-benzoisothiazolin-3-one
b) chloro-2-methyl-4-isothiazolin-3-one
c) 2-methyl-4-isothiazolin-3-one
d) 1,6-dihydroxy-2,5-dioxahexane
e) a solvent according to formula I.

In a preferred embodiment, besides the butyl polyglycol ethers according to the formula (I) used according to the invention, the compositions according to the invention can comprise up to 40% by weight, preferably up to 30% by weight, of further solvents. Such further solvents from the group of
glycols are, for example, ethylene glycol, diethylene glycol, triethylene glycol, tetraethylene glycol, polyethylene glycol, propylene glycol, dipropylene glycol, tripropylene glycol, polypropylene glycol,
terminally capped glycols are, for example, monoethylene glycol dimethyl ether (monoglyme), diethylene glycol dimethyl ether (diglyme), triethylene glycol dimethyl ether (triglyme), triethylene glycol diethyl ether, tetraethylene glycol dimethyl ether and tetraethylene glycol diethyl ether, propylene glycol phenyl ether, polyethylene glycol dibutyl ether;

polyethylene glycol diallyl ether; polyethylene glycol allyl methyl ether; polyalkylene glycols; polyalkylene glycol allyl methyl ether, alcohols are, for example, methanol, ethanol, n-propanol, isopropanol, n-butanol, isobutanol, t-butanol, n-pentanol, n-hexanol, 2-methoxyethanol, 2-butoxyethanol, 2-(2-butoxyethoxyl)ethanol, phenoxyethanol, 2-(2-butoxyethoxyl)ethanol, 3-methoxy-butanol, 1-methoxy-2-propanol, sec-butyl alcohol, tert-butyl alcohol, isobutyl alcohol, 2-ethylhexanol, 2-propoxyethanol, benzyl alcohol, phenethyl alcohol, 1,2,6-hexanetriol, alkanes are, for example, pentane, hexane, heptane, chlorinated alkanes are, for example, methylene chloride, ethylene dichloride;

aromatics are, for example, benzene, toluene, xylene;

nitriles is, for example, acetonitrile;

amide are, for example, dimethylformamide, N,N-dimethylacetamide, hexamethylphosphoramide;

ketones are, for example, acetone, ethyl methyl ketone, methyl isobutyl ketone, methyl isobutyl ketone, methyl amyl ketone, methyl isoamyl ketone, 2-butanone, ethers is, for example, isopropyl ether, acetates is, for example, ethyl acetate, propyl acetate, isopropyl acetate, butyl acetate, isobutyl acetate, 2-methoxyethyl acetate, 1-methoxy-2-propyl acetate, ethylene glycol diacetate, lactates are, for example, methyl lactate, ethyl lactate, phosphates are, for example, trihexyl(tetradecyl)phosphonium hexafluoro-phosphate, trihexyl(tetradecyl)phosphonium tetrafluorophosphate, amines are, for example, monoethanolamine, diethanolamine, triethanolamine, polyols are, for example, glycerol, trimethylolethane, trimethylolpropane, and also tetrahydrofuran, 1,4-dioxane, dimethyl sulfoxide, diethyl carbonate, propylene carbonate, pyridine, picoline, lutidine, collidine, cyclohexanone and/or water.

According to the invention, the biocidal compositions can comprise up to 80% by weight, preferably 5 to 60% by weight, particularly preferably up to 30% by weight, of one or more biocidal active substances and 10 to 99% by weight, preferably 15% by weight to 80% by weight, particularly preferably 20 to 70% by weight, of one or more of the above-mentioned butyl polyglycol ethers, according to the formula I, based on the finished biocidal compositions. These are usually used in weight amounts such that from 0.0001% by weight to 5% by weight, preferably 0.0002% by weight to 3% by weight, particularly preferably from 0.0005% by weight to 1% by weight, of the biocidal active substance(s), based on the substrate to be treated or the treated end product, are used.

The biocidal compositions according to the invention can, if appropriate, comprise emulsifiers or dispersants.

Suitable dispersants and emulsifiers are addition products of from 2 to 30 mol of ethylene oxide and/or up to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group; $C_{12}$-$C_{18}$-fatty acid mono- and diesters of addition products of from 1 to 30 mol of ethylene oxide onto glycerol, glycerol mono- and diesters and sorbitan mono- and diesters of saturated and unsaturated fatty acids having 6 to 22 carbon atoms and ethylene oxide addition products thereof; addition products of from 15 to 60 mol of ethylene oxide onto castor oil and/or hydrogenated castor oil; polyol and, in particular, polyglycerol esters, for example, polyglycerol polyricinoleate and polyglycerol poly-12-hydroxystearate. Preferred liquid fatty acid esters are PEG-10 polyglyceryl-2 laurate and polyglyceryl-2-sesquiisostearate.

Further suitable are ethoxylated and nonethoxylated mono-, di- or trialkyl phosphoric esters and alkylaryl phosphoric esters, for example isotridecyl phosphoric esters and salts thereof, tri-sec-butylphenol phosphoric esters and salts thereof and tristyryl-phenyl phosphoric esters and salts thereof.

Cationic emulsifiers, such as mono-, di- and trialkyl quats and polymeric derivatives thereof can also be used.

Likewise suitable are mixtures of compounds of two or more of these substance classes. The addition products of ethylene oxide and/or propylene oxide onto fatty alcohols, fatty acids, alkylphenols, glycerol mono- and diesters, and sorbitan mono- and diesters of fatty acids or onto castor oil are known commercially available products. These are homolog mixtures whose average degree of alkoxylation corresponds to the ratio of the quantitative amounts of ethylene oxide and/or propylene oxide and substrate with which the addition reaction is carried out.

The biocidal compositions according to the invention can comprise 0.1 to 40% by weight, preferably 1 to 30% by weight, particularly preferably 3 to 20% by weight, of one or more emulsifiers or dispersants, based on the finished biocidal compositions.

The biocidal compositions according to the invention can additionally comprise surfactants, thickeners, antigelling agents, solubility promoters, low-temperature protectants, antifoams, buffers, wetting agents, complexing agents, sequestrants, electrolytes, extenders, fragrances and dyes.

In a further embodiment, the compositions according to the invention can comprise anionic surfactants.

Preferred anionic surfactants are straight-chain and branched alkyl sulfates, alkylsulfonates, alkyl carboxylates, alkyl phosphates, alkyl sulfosuccinates and alkyl taurates, alkyl ester sulfonates, arylalkylsulfonates and alkyl ether sulfates.

Alkyl sulfates are water-soluble salts or acids of the formula $ROSO_3M$, in which R is preferably a $C_{10}$-$C_{24}$-hydrocarbon radical, particularly preferably an alkyl or hydroxyalkyl radical having 10 to 20 carbon atoms and especially preferably a $C_{12}$-$C_{18}$-alkyl or hydroxyalkyl radical. M is hydrogen or a cation, preferably an alkali metal cation (e.g. sodium, potassium, lithium) or ammonium or substituted ammonium, e.g. a methyl-, dimethyl- and trimethylammonium cation or a quaternary ammonium cation, such as tetramethylammonium and dimethylpiperidinium cation and quaternary ammonium cations derived from alkylamines, such as, ethylamine, diethylamine, triethylamine and mixtures thereof.

The alkyl ether sulfates are water-soluble salts or acids of the formula $RO(A)_mSO_3M$, in which R is preferably a unsubstituted $C_{10}$-$C_{24}$-alkyl or hydroxyalkyl radical, particularly preferably a $C_{12}$-$C_{20}$-alkyl or hydroxyalkyl radical and especially preferably a $C_{12}$-$C_{18}$-alkyl or hydroxyalkyl radical. A is an ethoxy or propoxy unit, m is a number greater than 0, typically between 0.5 and 6, particularly preferably between 0.5 and 3 and M is a hydrogen atom or a cation, preferably a metal cation (e.g. sodium, potassium, lithium, calcium, magnesium), ammonium or a substituted ammonium cation. Examples of substituted ammonium cations are methyl-, dimethyl-, trimethylammonium and quaternary ammonium cations, such as tetramethylammonium and dimethylpiperidinium cations, and also those which are derived from alkylamines, such as ethylamine, diethylamine, triethylamine or mixtures thereof. Examples which may be mentioned are $C_{12}$-$C_{18}$-alkyl polyethoxylate (1.0)sulfate, $C_{12}$-$C_{18}$-alkyl polyethoxylate (2.25)sulfate, $C_{12}$-$C_{18}$-alkyl polyethoxylate (3.0)sulfate, $C_{12}$-$C_{18}$-alkyl polyethoxylate (4.0)sulfate, where the cation is sodium or potassium.

Likewise suitable are alkylsulfonates with straight-chain or branched $C_6$-$C_{22}$-alkyl chains, for example primary paraffinsulfonates, secondary paraffinsulfonates, alkylarylsulfonates, for example linear alkylbenzenesulfonates with $C_5$-$C_{20}$-alkyl chains, alkylnaphthalenesulfonates, condensation products of naphthalenesulfonate and formaldehyde, lignosulfonate, alkyl ester sulfonates, i.e. sulfonated linear esters of $C_8$-$C_{20}$-carboxylic acids (i.e. fatty acids), $C_8$-$C_{24}$-olefinsulfonates, sulfonated polycarboxylic acids, prepared by sulfonation of the pyrrolysis products of alkaline earth metal citrates.

Further suitable anionic surfactants are chosen from alkyl glycerol sulfates, fatty acyl glycerol sulfates, oleyl glycerol sulfates, alkylphenol ether sulfates, alkyl phosphates, alkyl ether phosphates, isethionates, such as acyl isethionates, N-acyltaurides, alkyl succinamates, sulfosuccinates, in particular dinonyl or dioctyl sulphosuccinates, monoesters of these sulfosuccinates (particularly saturated and unsaturated $C_{12}$-$C_{18}$-monoesters) and diesters of the sulfosuccinates (particular saturated and unsaturated $C_{12}$-$C_{18}$-diesters), acyl sarcosinates, sulfates of alkyl polysaccharides, such as sulfates of alkyl polyglycosides, branched primary alkyl sulfates and alkyl polyethoxycarboxylates, such as those of the formula $RO(CH_2CH_2O)_kCH_2COO^-M^+$, in which R is a $C_8$-$C_{22}$-alkyl group, k is a number from 0 to 10 and M is a soluble salt-forming cation.

Suitable nonionic surfactants are preferably fatty alcohol ethoxylates, (alkyl polyethylene glycols), alkylphenol polyethylene glycols, alkyl mercaptan polyethylene glycols, fatty amine ethoxylates (alkylaminopolyethylene glycols), fatty acid ethoxylates (acyl polyethylene glycols), polypropylene glycol ethoxylates (e.g. Pluronics®), fatty acid alkylolamides (fatty acid amide polyethylene glycols), N-alkyl- and N-alkoxypolyhydroxy fatty acid amides, alkyl polysaccharides, sucrose esters, sorbitol esters and polyglycol ethers.

Suitable amphoteric surfactants are preferably amphoacetates, particularly preferably monocarboxylates and dicarboxylates, such as cocoamphocarboxypropionate, cocoamidocarboxypropionic acid, cocoamphocarboxyglycinate (or also referred to as cocoamphodiacetate) and cocoamphoacetate.

Suitable cationic surfactants are, for example, di($C_{10}$-$C_{24}$)-alkyldimethylammonium chloride or bromide, preferably di($C_{12}$-$C_{18}$)-alkyldimethylammonium chloride or bromide; ($C_{10}$-$C_{24}$)-alkyldimethylethylammonium chloride or bromide; ($C_{10}$-$C_{24}$)-alkyl-trimethylammonium chloride or bromide, preferably cetyltrimethylammonium chloride or bromide and ($C_{20}$-$C_{22}$)-alkyltrimethylammonium chloride or bromide; ($C_{10}$-$C_{24}$)-alkyldimethylbenzylammonium chloride or bromide, preferably ($C_{12}$-$C_{18}$)-alkyl-dimethylbenzylammonium chloride; N—($C_{10}$-$C_{18}$)-alkylpyridinium chloride or bromide, preferably N—($C_{12}$-$C_{16}$)-alkylpyridinium chloride or bromide; N—($C_{10}$-$C_{18}$)-alkylisoquinolinium chloride, bromide or monoalkyl sulfate; N—($C_{12}$-$C_{18}$)-alkylpolyoylamino-formylmethylpyridinium chloride; N—($C_{12}$-$C_{18}$)-alkyl-N-methylmorpholinium chloride, bromide or monoalkyl sulfate; N—($C_{12}$-$C_{18}$)-alkyl-N-ethylmorpholinium chloride, bromide or monoalkyl sulfate; ($C_{16}$-$C_{18}$)-alkylpentaoxyethylammonium chloride; diisobutylphenoxyethoxyethyldimethylbenzylammonium chloride; salts of N,N-diethylaminoethylstearylamide and -oleylamide with hydrochloric acid, acetic acid, lactic acid, citric acid, phosphoric acid; N-acylaminoethyl-N,N-diethyl-N-methyl-ammonium chloride, bromide or monoalkyl sulfate and N-acylaminoethyl-N,N-diethyl-N-benzylammonium chloride, bromide or monoalkyl sulfate, where acyl is preferably stearyl or oleyl.

The biocidal compositions according to the invention can comprise 0.1 to 40% by weight, preferably 1 to 30% by weight, particularly preferably 3 to 20% by weight, of one or more surfactants, based on the finished biocidal compositions.

The thickeners used are preferably carboxymethylcellulose and hydroxyethyl-cellulose, xanthan gum, guar guar, agar agar, alginates and tyloses, also higher molecular weight polyethylene glycol mono- and diesters of fatty acids, hydrogenated castor oil, salts of long-chain fatty acids, for example sodium, potassium, aluminum, magnesium and titanium stearates or the sodium and/or potassium salts of behenic acid, but also polyacrylates, polyvinyl alcohol and polyvinylpyrrolidone, and also polysaccharides. Likewise suitable are copolymers based on acryloyldimethyltauric acid, as described in EP-A-1 060 142, EP-A-1 028 129, EP-A-1 116 733.

The thickeners can be used in the biocidal compositions according to the invention preferably in amounts of from 0.01 to 5% by weight and in particular in amounts of from 0.5 to 2% by weight, based on the finished biocidal compositions.

Suitable solubility promoters are sodium toluenesulfonate, sodium cumenesulfonate, sodium xylenesulfonate, alkanephosphonic acids and alkenyldicarboxylic acids, and anhydrides thereof.

Low-temperature stabilizers which may be used are all customary substances which can be used for this purpose. By way of example, reference may be made to urea, glycerol and propylene glycol. Hydrogen peroxide may be any inorganic peroxide which releases hydrogen peroxide in aqueous solution, such as, for example, sodium perborate (monohydrate and tetrahydrate) and sodium percarbonate.

Suitable antifoams are fatty acid alkyl ester alkoxylates; organopolysiloxanes, such as polydimethylsiloxanes and mixtures thereof with microfine, optionally silanized silica; paraffins, waxes and microcrystalline waxes and mixtures thereof with silanized silica. Also advantageous are mixtures of different foam inhibitors, for example those of silicone oil, paraffin oil and/or waxes.

Suitable buffers are all customary acids and salts thereof. Preferably, mention may be made of phosphate buffers, carbonate buffers, citrate buffers.

Wetting agents which can be used are alcohol ethoxylates/propoxylates. Furthermore, the mixtures according to the invention preferably comprise neutralizing agents and extenders for adjusting the composition to a viscosity of from 100 to 2000 mPas, preferably of about 600 mPas. Preferred extenders are inorganic salts, particularly preferably ammonium or metal salts, in particular of halides, oxides, carbonates, hydrogen carbonates, phosphates, sulfates and nitrates, in particular sodium chloride. As neutralizing agent, preference is given to NaOH and KOH.

As electrolyte, the compositions according to the invention can comprise inorganic and organic salts. Alkali metal, alkaline earth metal, metal or ammonium halides, nitrates, phosphates, carbonates, hydrogen carbonates, sulfates, silicates, acetates, oxides, citrates or polyphosphates are suitable. For example, $CaCl_2$, $MgCl_2$, $LiCl$, $KCl$, $NaCl$, $K_2SO_4$, $K_2CO_3$, $MgSO_4$, $Mg(NO_3)_2$, $ZnCl_2$, $ZnO$, $MgO$, $ZnSO_4$, $CuSO_4$, $Cu(NO_3)_2$ are preferably used.

Suitable organic salts are ammonium or metal salts, preferably of glycolic acid, lactic acid, citric acid, tartaric acid, mandelic acid, salicylic acid, ascorbic acid, pyruvic acid, fumaric acid, retinoic acid, sulfonic acids, benzoic acid, kojic acid, fruit acid, malic acid, gluconic acid, galacturonic acid. As electrolyte, the compositions can also comprise mixtures of different salts.

The compositions according to the invention can comprise electrolytes in amounts of from 0.01 to 50% by weight, preferably 0.1 to 20% by weight, particularly preferably 0.5 to 10% by weight, based on the biocidal composition.

Suitable sequestrants are, for example, sodium tripolyphosphate (STPP), ethylenediaminetetraacetic acid (EDTA), salts thereof, nitrilotriacetic acid (NTA), polyacrylate, phosphonate, for example 1-hydroxyethane-1,1-diphosphonic acid (HEDP), salts of polyphosphoric acids, such as ethylenediaminetetramethylenephosphonic acid (EDTMP) and diethylenetriaminepentamethylenephosphonic acid (DTPMP), oxalic acid, oxalic salt, citric acid, zeolite, carbonates and polycarbonates.

Suitable complexing agents are phosphonates, aminophosphonates and aminocarboxylates.

The biocidal compositions according to the invention are preferably used for preserving paints, coatings, polymer emulsions, cooling lubricants, metalworking auxiliaries, crop protection formulations, construction chemicals, cleaners, plastic and adhesives.

Moreover, the biocidal compositions according to the invention can be used directly or in dilution as disinfectants.

Moreover, the biocidal compositions according to the invention can be incorporated into coating materials for surfaces. Surfaces which are coated with such coating materials are thereby given a biocidal finish.

For all of the specified applications, the use amounts of the biocidal active substances already given apply.

The biocidal formulations preferably have a pH of from 1 to 13, particularly preferably 7 to 12, in particular 8 to 10.

EXAMPLES

The examples below serve to illustrate the invention in more detail. Unless stated otherwise, all of the percentages are percentages by weight.

TABLE 1

Storage stability of 1,2-benzoisothiazolin-3-one, Na salt in various butyl glycol ethers for a storage period of 14 days

| Example | Biocidal active substance | Solvent | −5° C. | +20° C. | +50° C. |
|---|---|---|---|---|---|
| 1 | 1,2-Benzoisothiazolin-3-one Na | butyl glycol | solid, considerable crystal growth | clear, no crystals | clear, no crystals |
| 2 | 1,2-Benzoisothiazolin-3-one Na | butyl diglycol | solid, considerable crystal growth | clear, no crystals | clear, no crystals |
| 3 | 1,2-Benzoisothiazolin-3-one Na | butyl triglycol | clear, no crystals | clear, no crystals | clear, no crystals |
| 4 | 1,2-Benzoisothiazolin-3-one Na | butyl polyglycol* | clear, no crystals | clear, no crystals | clear, no crystals |

*butyl polyglycol: homolog mixture of 75% by weight of n-butyl triglycol, 20% by weight of n-butyl tetraglycol, 3% by weight of n-butyl pentaglycol, 2% by weight of n-butyl diglycol Example 5

For solutions of biocidal active substances, a particularly favorable viscosity behavior was found when the biocidal active substances are dissolved together with hydroxides in butyl polyglycol. A particularly advantageous formulation using 1,2-benzoisothiazolin-3-one Na salt was composed as follows:
26.67 g Nipacide BIT (75% strength)
10.80 g NaOH (49% strength)
62.53 g butyl polyglycol Butyl polyglycol and NaOH were heated to about 60-70° C. with stirring. Following the addition of Nipacide BIT (1,2-benzoisothiazolin-3-one), the mixture was homogenized until a clear solution has formed.

The solution had a viscosity of 26.6 mPa·s at 40° C., 69.3 mPa·s at 20° C., 192 mPa·s at 5° C., 280 mPa·s at 0° C. and 408 mPa·s at −5° C.

TABLE 2

| Example | Biocidal active substance | Solvent | −5° C. | +20° C. | +50° C. |
|---|---|---|---|---|---|
| 6 | 2-Bromo-2-nitropropanediol | butyl glycol | solid, considerable crystal growth | clear, no crystals | clear, no crystals |
| 7 | 2-Bromo-2-nitropropanediol | butyl diglycol | solid, considerable crystal growth | clear, no crystals | clear, no crystals |

TABLE 2-continued

| Example | Biocidal active substance | Solvent | −5° C. | +20° C. | +50° C. |
|---|---|---|---|---|---|
| 8 | 2-Bromo-2-nitropropanediol | butyl triglycol | clear, no crystals | clear, no crystals | clear, no crystals |
| 9 | 2-Bromo-2-nitropropanediol | butyl polyglycol* | clear, no crystals | clear, no crystals | clear, no crystals |
| 10 | 1,2-Dibromo-2,4-dicyanobutane | butyl glycol | solid, considerable crystal growth | clear, no crystals | clear, no crystals |
| 11 | 1,2-Dibromo-2,4-dicyanobutane | butyl diglycol | solid, considerable crystal growth | clear, no crystals | clear, no crystals |
| 12 | 1,2-Dibromo-2,4-dicyanobutane | butyl triglycol | clear, no crystals | clear, no crystals | clear, no crystals |
| 13 | 1,2-Dibromo-2,4-dicyanobutane | butyl polyglycol* | clear, no crystals | clear, no crystals | clear, no crystals |

*butyl polyglycol means the composition given below table 1

The invention claimed is:

1. A composition comprising
a) 5 to 80% by weight of 1,2-benzoisothiazolin-3-one and/or its alkali metal or ammonium salt,
b) 15 to 80% by weight of at least one solvent according to the formula I $$R-(O-CH_2-CH_2)_x-O-H \quad (I)$$

wherein
R is a linear or branched butyl group and
x is a number from 3 to 10.

2. A composition as claimed in claim 1, wherein R is n-butyl.

3. A composition as claimed in claim 1, wherein x is a number from 3 to 6.

4. A composition as claimed in claim 1, wherein the at least one solvent of the formula I is a mixture which comprises 50% by weight or more of triethylene glycol butyl ether and 10% by weight or more of tetraethylene glycol butyl ether.

5. A composition as claimed in claim 1, wherein the at least one solvent is a mixture comprising less than 20% by weight of diethylene glycol butyl ether.

6. A composition as claimed in claim 1, further comprising
a) chloro-2-methyl-4-isothiazolin-3-one,
b) 2-methyl-4-isothiazolin-3-one, and
c) 1,6-dihydroxy-2,5-dioxahexane.

7. A method for producing a solution of a biocidilly active substance, comprising dissolving 5 to 80 wt.-% of benzisothiazolin-2-one and/or its alkali or ammonium salt in 15 to 80 wt.-% of at least one solvent according to formula I $$R-(O-CH_2-CH_2)_x-O-H \quad (I)$$

wherein
R is a linear or branched butyl group and
x is a number from 30 to 10.

* * * * *